United States Patent [19]

Forte

[11] 4,306,550
[45] Dec. 22, 1981

[54] COMBINATION INCLUDING FEMORAL RASP AND CALCAR FACING REAMER

[75] Inventor: Mark R. Forte, Montville Township, Morris County, N.J.

[73] Assignee: Minnesota Mining and Manufacturing Company, St. Paul, Minn.

[21] Appl. No.: 119,166

[22] Filed: Feb. 6, 1980

[51] Int. Cl.³ ...................... A61F 5/04; A61F 17/32; B26B 7/00
[52] U.S. Cl. ................................ 128/92 E; 128/305; 30/276
[58] Field of Search .......... 128/92 E, 92 EB, 92 EC, 128/92 BB, 305; 3/1.9, 1.91, 1.912, 1.913; 30/276

[56] References Cited

U.S. PATENT DOCUMENTS

| 3,867,932 | 2/1975 | Huene | 128/92 E |
| 4,124,026 | 11/1978 | Berner et al. | 128/92 E X |
| 4,246,895 | 1/1981 | Rehder | 128/92 E |

OTHER PUBLICATIONS

"Howmedica Total Hip and Endoprosthesis Systems", Catalogue, Aug. 1978, pp. 7, 11C and 28.

Primary Examiner—Stephen C. Pellegrino
Attorney, Agent, or Firm—Cruzan Alexander; Donald M. Sell; William L. Huebsch

[57] ABSTRACT

A combination of tools and methods used to prepare a socket in a femur for receiving a femoral prosthesis including a rasp having a cutting portion and a pilot post portion, a handle assembly with a chuck for releasably engaging the pilot post portion to facilitate working the rasp into a femur, and a cutter device adapted to be journaled on the pilot post and power driven to surface the calcar adjacent the socket. After a socket is formed in the femur by use of a rasp and handle assembly, the rasp is left in the socket, the handle assembly is removed, and the cutter is journaled over the pilot post and rotated by a drive apparatus.

5 Claims, 6 Drawing Figures

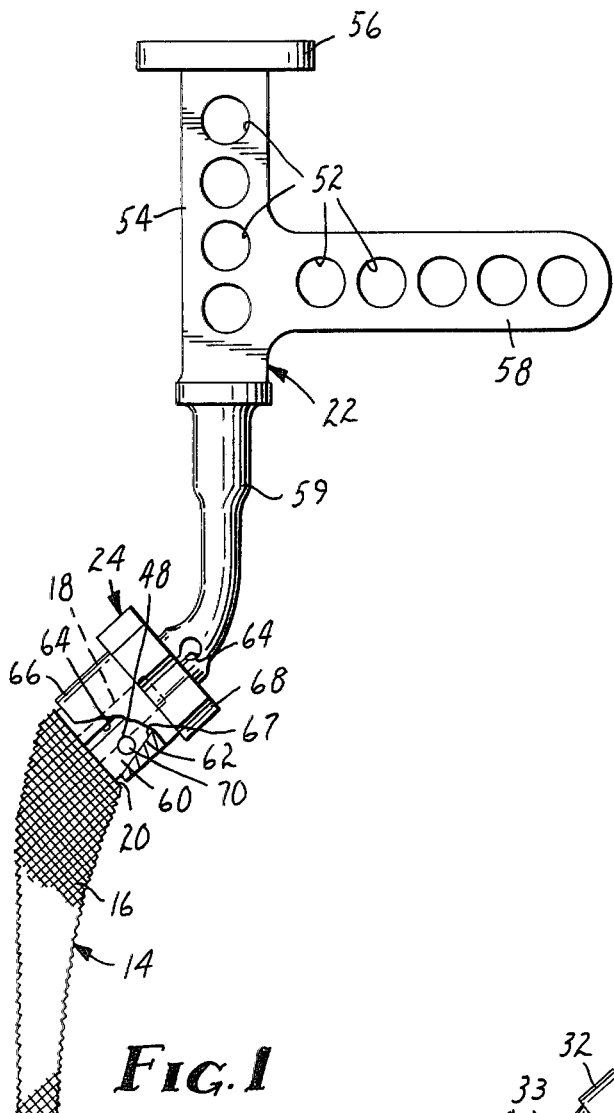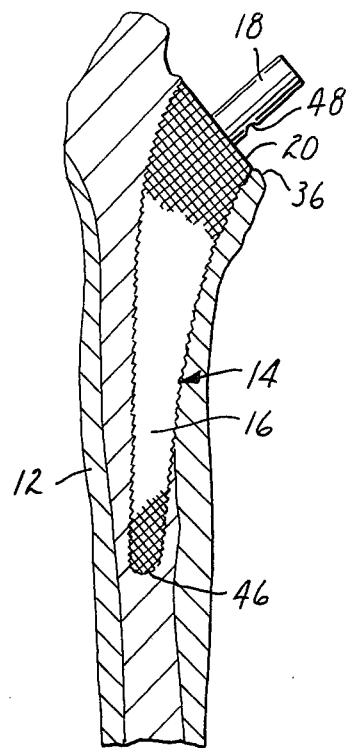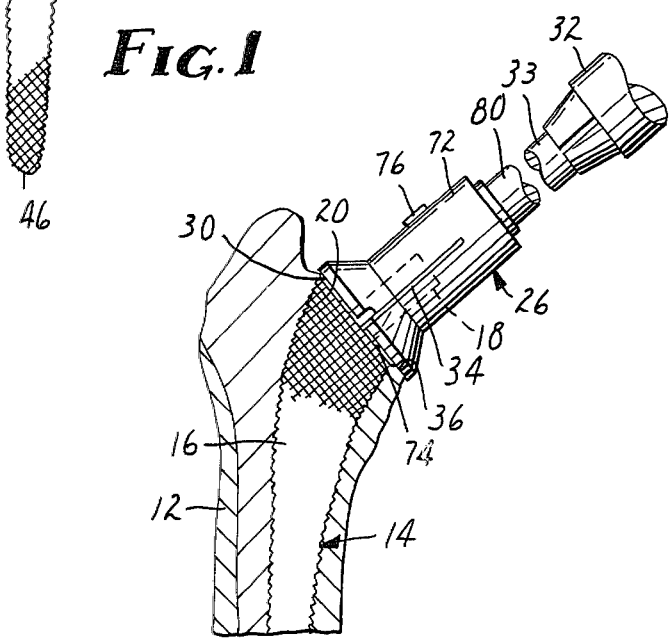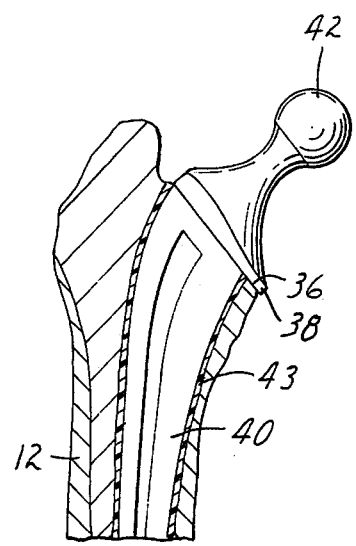
FIG. 1
FIG. 2
FIG. 3
FIG. 4

COMBINATION INCLUDING FEMORAL RASP AND CALCAR FACING REAMER

BACKGROUND OF THE INVENTION

This invention relates to combinations of tools and methods used to prepare a socket in a femur for receiving a femoral prosthesis.

One common type of femoral prosthesis includes a stem portion adapted to be inserted and fixated (as by cement) in a socket rasped into the proximal femur of a patient, a ball portion adapted to project and engage a cup implanted in the pelvis of the patient, and a collar between the stem and ball portions adapted to rest against the calcar forming the medial wall portion of the femur at the inlet to the socket to help bear the load applied to the femur through the prosthesis. Some experts feel that the fit between the collar and the calcar must be very precise, or such loads will be borne only by the stem portion; and that this lack of loading on the calcar of the inlet to the socket will cause it to resorb or be dissolved by the body, thereby weakening the side walls forming the socket that support the stem portion so that the stem portion may eventually loosen in the femur.

For this reason, a calcar rasp set is presently available that includes a guide member including a stem portion shaped like the stem portion of a femoral prosthesis and a pilot post portion projecting from its stem portion; and a rotary rasp adapted to be journaled on the pilot post portion and manually rotated. After a socket is formed in a femur through the use of a conventional rasp having a handle permanently attached at one end, and before the stem portion of the femoral prosthesis is positioned and fixated in the socket, the stem portion of the guide member is inserted into the socket so that the pilot post portion projects from the femur, and the rotary rasp is journaled on the pilot post portion and manually rotated so that the rasp faces the surface of the calcar around the inlet to the socket.

These tools and method of facing the calcar around the socket may not be as precise as may be desired, however, since any differences in size between the stem portion of the guide member and the socket could cause the stem portion of the guide member to be off center in the socket and the resultant facing of the calcar to be inaccurate with respect to the collar of a femoral prosthesis subsequently fixated in the socket.

SUMMARY OF THE INVENTION

According to the present invention there is provided a combination for use in preparing a socket in a human femur to receive a femoral prosthesis, which combination can more accurately surface calcar around the socket for precise engagement by a collar on the prosthesis.

The combination according to the present invention includes (1) an elongated rasp having a cutting portion of a known elongate, slightly curved design tapered from a first end toward a second end and having cutting teeth on its surface, and a pilot post portion projecting from the first end of the cutting portion; (2) a handle assembly including chuck means adapted for releasably engaging the pilot post portion and including portions adapted to be manually engaged and hammered against to facilitate working the rasp into a femur; and (3) a cutter having walls defining a cylindrical bore opening through a first end and being adapted to be journaled on the pilot post portion, a second end adapted to be releasably engaged and rotated by an externally powered drive apparatus, and a cutter blade fixed along the first end of the cutter generally radially of the axis of the cylindrical bore. After a socket is formed in a femur by use of the handle assembly attached to the rasp, the rasp is left in the socket, the handle assembly is removed, and the cutter is journaled over the pilot post portion and rotated by the drive apparatus to surface the calcar adjacent the opening to the socket. Since the rasp fits exactly in the socket it forms, such surfacing will be very precise with respect to the socket to ensure a good fit between the faced surface of the calcar and the collar portion of a femoral prosthesis subsequently fixated in the socket.

BRIEF DESCRIPTION OF THE DRAWING

The present invention will be further described with reference to the accompanying drawing wherein like numbers refer to like parts in the several views, and wherein FIG. 1 is a side view of a rasp and a handle assembly included in the combination according to the present invention, which rasp and handle assembly are shown coupled together;

FIG. 2 is a side view of the rasp of FIG. 1 shown positioned in a socket formed in a sectional fragment of a human femur and from which rasp the handle assembly shown in FIG. 1 has been removed;

FIG. 3 is a side view similar to FIG. 2 but additionally showing a cutter included in the combination journaled on a pilot post portion and being rotated via a fragment of a rotary drive member to face the calcar of the femur around the inlet to the socket;

FIG. 4 is a side view of the sectional fragmentary femur of FIG. 2 showing a femoral prosthesis cemented in the socket formed by the rasp and cutter.

DESCRIPTION OF THE PREFERRED EMBODIMENT

Figure 5:
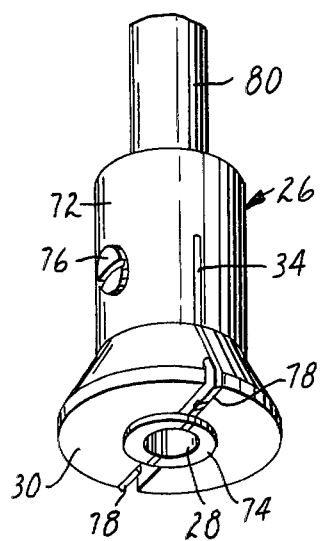
FIGS. 5 and 6 are perspective and side views respectively of the cutter shown in FIG. 3.
Figure 6:
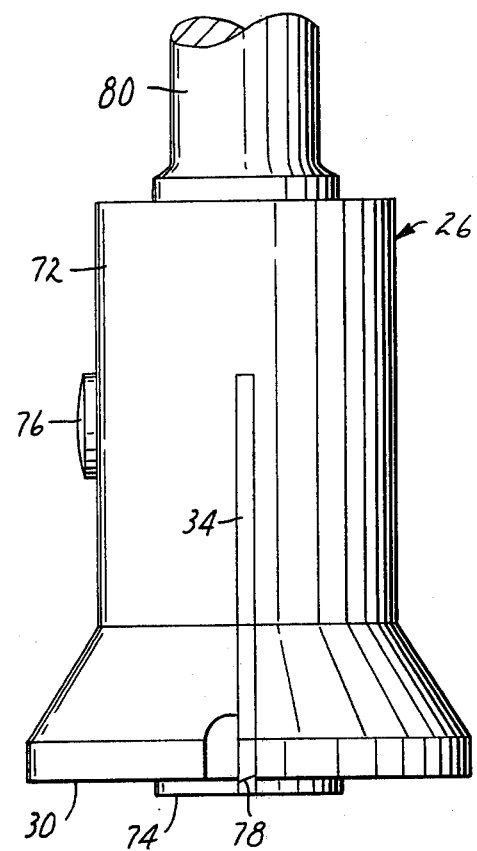

Referring now to the drawing there is shown a combination according to the present invention for preparing a socket in a human femur 12 after the proximal head and neck parts of the femur 12 have been resected, comprising a rasp 14 (FIGS. 1 and 2) having an elongate cutting portion 16 with a shape corresponding to the shape of a socket desired to be formed in the femur 12, and a generally cylindrical pilot post portion 18 projecting from a first end 20 of the cutting portion 16; a handle assembly 22 (FIG. 1) including chuck means or a chuck assembly 24 adapted for releasably engaging the pilot post portion 18 to assemble the handle assembly 22 and rasp 14 together in a predetermined relationship; and a cutter 26 (FIGS. 3, 5 and 6) having walls defining a cylindrical bore 28 communicating through a first end 30 of the cutter 26 and adapted to be journaled around the pilot post portion 18 on the rasp 14.

After the rasp 14 is used in combination with the handle assembly 22 to form a socket, the rasp 14 is left in the socket and the handle assembly 22 is removed (FIG. 2) so that the cutter 26 can then be journaled on the pilot post portion 18 (FIG. 3) and rotated via a rotary drive mechanism 32 (e.g., an air motor) releasably engaged with a second end 33 of the cutter 26 so that a cutting blade 34 projecting along the first end 30 of the cutter 26 will face a surface 36 of the calcar around the opening to the socket. Thus the calcar is precisely faced around the socket so that, as is shown in FIG. 4, a flange 38 between a stem portion 40 and a projecting ball 42 of a femoral prosthesis fixated in the femur 12 by a cement layer 43 will fit precisely on and bear under load against the faced surface 36 of the calcar to restrict resorption of the calcar adjacent the socket.

The cutting portion 16 of the rasp 14 has a known elongate shape which is tapered and slightly curved in one plane toward a second end 46 from its first end 20, and has sharp cutting teeth projecting from all of its surfaces except a planar surface at its first end 20 normal to which surface the pilot post portion 18 projects. The axis of the pilot post 18 is disposed at an angle of about 45 degrees with respect to the centerline of the cutting portion 16 adjacent its second end 46. The pilot post portion 18 is generally cylindrical but has a transverse slot 48 along its length that is adapted to be engaged by a portion of the chuck assembly 24 to orient the rasp 14 in a predetermined relationship with respect to the handle assembly 22, as will later be explained.

The handle assembly 22 includes a generally L-shaped portion of a generally rectangular cross section which is lightened by a plurality of through apertures 52, has a first leg 54 with a generally circular plate 56 fixed transversely at its end, which plate 56 is adapted either to be hammered against or will facilitate grasping of the handle assembly 22, and a second leg 58 disposed at a right angle with respect to the first leg 54 and having a rounded end portion adapted to afford manual engagement of the handle assembly 22 while it is being used to manipulate the rasp 14. A stepped, generally cylindrical angled portion 59 of the handle assembly 22 is attached to the L-shaped portion at the intersection of the legs 54 and 58 with its adjacent portion generally aligned with the first leg 54, and has a distal end portion on which the chuck assembly 24 is supported and which is bent in the common plane of the legs 54 and 58 at an angle generally equal to the angle between the pilot post portion 18 and the part of the rasp 14 adjacent its first end 46 (i.e., about 45 degrees) so that when the rasp 14 is engaged by the chuck assembly 24 as illustrated, with the plane in which the rasp 14 is curved coplanar with the common plane through the legs 54 and 58, forces applied to the plate 56 will be applied in a direction generally parallel to the longitudinal direction of the rasp 14 adjacent its second end 46.

The chuck assembly 24 comprises a collar 60 having an axis extending between first and second ends, which collar 60 has its first end fixed to the end of the cylindrical part 59 opposite the L-shaped portion of the handle assembly 22, a generally cylindrical socket opening through its second end adapted to freely receive the pilot post portion 18, a frusto-conical outer surface 62, and a transverse slot 64 bisecting it into two portions. A knob 66 is positioned around the collar 60 and has a frustroconical inner surface 67 adapted to engage the outer surface 62 of the collar 60 and move the portions of the collar 60 together upon axial movement of the knob 66 from a first to a second portion along the collar 60. The collar 60 and knob 66 have means or threaded portions in engagement with each other for causing axial movement of the knob 66 between its first and second positions upon manual rotation of the knob 66 about the collar 60, which is facilitated by a fluted outer portion 68 of the knob 66. A locking member or pin 70 extends transverse of the collar 60, projects into the socket in the collar 60, and is adapted to nest in the slot 48 transverse of the pilot post portion 18 when the pilot post portion 18 is positioned in the socket in the collar 60 and the portions of the collar 60 are moved together to thus orient the rasp 14 in the predetermined relationship with respect to the handle assembly 22 described above with the plane in which the rasp 14 is curved coplanar with the common plane through the legs 54 and 58, and with the second end 46 of the rasp pointing away from the handle assembly 22.

The cutter 26 comprises a ridged generally bell-shaped housing 72 and a cylindrical polymeric bushing 74 (FIGS. 5 and 6) centered in the housing 72 and defining the cylindrical bore 28 of the cutter. The cutter blade 34 is fixed in a transverse slot in the housing 72 via a set screw 76 with sharpened aligned edge portions 78 of the blade 34 extending radially in opposite directions away from the bushing 74. A ridged shaft 80 is coaxially fixed on the end of the housing 72 opposite the first end of the cutter 26 and has its end 33 (FIG. 3) opposite the housing 72 shaped for engagement by the drive mechanism 32.

I claim:

1. A combination for use in preparing a human femur for the implantation of a femoral prosthesis, said assembly comprising:

a rasp comprising an elongate cutting portion tapered and slightly curved from a first toward a second end, having cutting teeth projecting from its surface and being adapted to be worked second end first into the medullary canal of said femur to prepare a socket adapted to receive a stem portion of the femoral prosthesis, and a generally cylindrical pilot post portion projecting from the first end of said cutting portion;

a handle assembly comprising chuck means adapted for releasable engagement with said pilot post portion with said rasp in a predetermined orientation with respect to said handle assembly, and a handle portion adapted to be manually engaged and hammered against to facilitate use of the rasp to form the socket; and a cutter having an axis extending between first and second ends, walls defining a cylindrical bore opening through said second end and adapted for close-fitting engagement around said pilot post portion, a generally radially extending cutter blade projecting along said second end, and means at said first end adapted for engagement by a drive apparatus to rotate said cutter about said pilot post portion so that said cutter blade can surface the calcar surface around a socket in a femur in which said rasp is positioned.

2. A combination according to claim 1, wherein said pilot post portion of said rasp has a transverse slot, said chuck means comprises a collar having an axis extending between first and second ends, said collar being fixed to said handle portion at said first end, having a socket opening through said second end adapted to freely receive said pilot post portion, a frustroconical outer surface, and a transverse slot bisecting the said collar into two portions; a knob around said collar having a frustroconical inner surface adapted to engage the outer surface of said collar and move the portions of said collar together upon axial movement of said knob from a first to a second portion along said collar, means in engagement between said knob and said collar for causing axial movement of said knob between said first and second positions upon rotation of said knob about said collar; and a locking member transverse of said collar and projecting into said collar adapted to nest in the transverse slot of said pilot post portion to position said rasp in said predetermined orientation with respect to said handle assembly when said pilot post portion is positioned in said socket and said portions are moved together.

3. A combination according to claim 1 wherein said cutter further comprises a ridged housing defining said first and second ends and a polymeric bushing centered in said housing and defining said cylindrical bore, and said cutter blade is fixed in said ridged housing at said second end and has sharpened, aligned edge portions extending radially in opposite directions away from said bushing.

4. A combination according to claim 1 wherein said handle assembly includes a generally L-shaped portion having first and second legs disposed at a right angle to each other, a transverse plate fixed at the end of said first leg and adapted to be grasped or hammered against, an angled portion joined to said L-shaped part at the intersection of said legs, having a part adjacent said L-shaped portion aligned with said first leg, and a second part on which said chuck means is fixed disposed at an obtuse angle in a plane defined by the legs of said L-shaped portion; said chuck means orients said rasp with the curve in said cutter portion generally in the plane defined by said legs and the first end of said cutting portion directed away from said handle assembly.

5. A method for preparing a socket adapted to receive a femoral prosthesis in a human femur, comprising the steps of:
providing a combination including:
a rasp comprising an elongate cutting portion tapered from a first toward a second end and having cutting teeth projecting from its surface, and a generally cylindrical pilot post portion projecting from the first end of the cutting portion;
a handle assembly comprising means adapted for releasable engagement with the pilot post portion with the rasp in a predetermined orientation with respect to said handle assembly and a handle portion adapted to be manually engaged and hammered against; and
a cutter having walls defining a cylindrical bore opening through a second end and adapted for close-fitting engagement around the pilot post portion, a generally radially extending cutter blade projecting along said second end, and means at said first end adapted for engagement by a drive apparatus to rotate said cutter about the pilot post portion;
attaching the handle assembly to the pilot post portion of the rasp;
manually working the cutting portion of the rasp into the medullary canal of the femur to form a socket;
removing the handle assembly from the pilot post portion of the rasp while leaving the rasp in the socket;
journaling the cutter on the pilot post portion;
rotating the cutter to face the calcar at the inlet to the socket; and
removing the rasp from the socket.

* * * * *